United States Patent [19]

Käsbauer et al.

[11] Patent Number: 5,672,719
[45] Date of Patent: Sep. 30, 1997

[54] PROCESS FOR THE PREPARATION OF ISOBENZOFURANDIONES

[75] Inventors: Josef Käsbauer, Wermelskirchen; Helmut Fiege, Leverkusen, both of Germany

[73] Assignee: Bayer Aktiengesellschaft, Leverkusen, Germany

[21] Appl. No.: 528,388

[22] Filed: Sep. 13, 1995

[30] Foreign Application Priority Data

Jul. 24, 1995 [DE] Germany ............... 195 26 923.3

[51] Int. Cl.$^6$ ............... C07D 307/77; C07D 307/89
[52] U.S. Cl. ............... 549/240; 549/247
[58] Field of Search ............... 549/240, 247

[56] References Cited

FOREIGN PATENT DOCUMENTS

| 0158000 | 10/1985 | European Pat. Off. . | |
|---|---|---|---|
| 62-148450 | 7/1987 | Japan . | |
| 62148450 | 7/1987 | Japan ............... | C07C 63/16 |

OTHER PUBLICATIONS

JAPIO AN–87–148450, Abstract of JP–62,148,450 Jul. 2, 1987.
WPAT AN–87–224332/32, Abstract of JP–62,148,450 Jul. 2, 1987.
Chemical Abstracts, vol. 105, abstract no. 97266p, p. 615, (1986).
Chemical Abstracts, vol. 106, abstract No. 102704g, p. 1, (1987).
Chemical Abstracts, vol. 109, abstract No. 92690v, p. 679, (1988).
Chemical Abstracts, vol. 108, abstract No. 37393e, (1988).
Chemical Abstracts, vol. 110, abstract No. 213398n, (1989).

*Primary Examiner*—Matthew V. Grumbling
*Assistant Examiner*—Brenda Coleman
*Attorney, Agent, or Firm*—Sprung Horn Kramer & Woods

[57] ABSTRACT

Isobenzofurandiones are obtained in particularly advantageous manner by the dehydrogenation of tetrahydroisobenzofurandiones in the presence of catalysts at elevated temperature by a process in which distilled tetrahydroisobenzofurandiones are heated to temperatures of between 120° and 300° C. in the presence of supported palladium and/or platinum catalysts and in the presence of maleic acid derivatives in a trickle-phase or liquid-phase procedure, the temperature in the liquid-phase procedure being increased at a rate of 0.6° to 3° C. per minute above 80° to 110° C.

8 Claims, No Drawings

PROCESS FOR THE PREPARATION OF ISOBENZOFURANDIONES

The present invention relates to an improved process for the preparation of isobenzofurandiones by the dehydrogenation of tetrahydroisobenzofurandiones in the presence of supported palladium and/or platinum catalysts.

The aromatization of tetrahydroisobenzofurandiones to isobenzofurandiones via cleavage reactions such as dehydrogenation or hydrodehalogenation is known. Of particular interest is the dehydrogenation of 5-methyl-tetrahydroisobenzofuran-1,3-dione to 5-methyl-isobenzofuran-1,3-dione, a precursor for plant protection agents (see e.g. European patent application A-1 158 000).

If the catalyst is palladium on an aluminium oxide support, dehydrogenation at 300° C. in the absence of a hydrogen acceptor is accompanied by hydrogenation to the hexahydro product (see C.A. 105:97266, 106:102704 and 109:92690).

The selectivity has been improved with other educts by the addition of hydrogen acceptors. Thus, in the palladium-catalysed dehydrogenation of diethyl 4-methyl-tetrahydrophthalate at 210° C. with the addition of diethyl maleate (see C.A. 108:37393e), a yield of diethyl 4-methylphthalate of 86.7% of theory can be achieved. Presumably the hexahydro derivative is formed with a yield of 13% of theory because, in the comparative experiment without the addition of maleic acid ester, it is formed with a yield of 56% of theory. The process has the disadvantage that diethyl maleate has to be used in excess (240 mol %) and that fumarates are formed from the excess at the reaction temperatures. Because of their sublimation behaviour, fumarates interfere with the working-up and have to be separated from the diethyl succinate formed by the uptake of hydrogen.

The addition of propylene in the dehydrogenation of methyl-tetrahydroisobenzofuran-1,3-dione led to a yield of desired product of 85% of theory (see C.A. 110: 213398). However, the introduction of propylene into a melt at a temperature of ca. 200° C. is very expensive in safety terms on the industrial scale and is therefore extremely uneconomic. Here too, the yield is in need of improvement.

The object of the present invention was therefore to provide a process which mitigates the disadvantages of the state of the art and enables isobenzofurandiones to be prepared in a technically simple manner with high yields by catalytic dehydrogenation.

A process has now been found for the preparation of isobenzofurandiones by the dehydrogenation of tetrahydroisobenzofurandiones in the presence of catalysts at elevated temperature, which is characterized in that distilled tetrahydroisobenzofurandiones are heated to temperatures of between 120° and 300° C. in the presence of supported palladium and/or platinum catalysts and in the presence of maleic acid derivatives in a trickle-phase or liquid-phase procedure, the temperature in the liquid-phase procedure being increased at a rate of 0.6° to 3° C. per minute above 80° to 110° C.

The process according to the invention can be carried out using e.g. tetrahydroisobenzofurandiones of the formula (I):

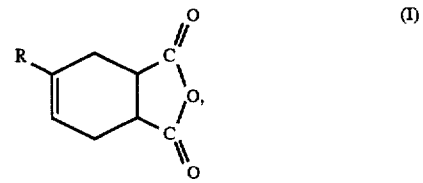

in which

R represents hydrogen or $C_1$–$C_6$-alkyl. R is preferably methyl.

Compounds of the formula (I) are readily accessible by a Deils-Alder synthesis from maleic anhydride and the appropriate diolefins. If undistilled tetrahydroisobenzofurandiones are used, the reaction rate slows down and the attainable yield is reduced (see Comparative Example 2).

Examples of suitable catalysts are supported palladium and/or platinum catalysts known per se, for example those containing 0.1 to 10% by weight of palladium and/or platinum on aluminium oxide, silicon dioxide, silicic acid, kieselguhr, silicates or charcoal. The catalysts preferably contain 1 to 8% by weight of palladium and/or platinum on aluminium oxide or activated charcoal. Supported palladium catalysts are particularly preferred.

The palladium and/or platinum can be used not only in metallic form but also in the form of compounds. In general, such compounds are reduced to the metal under the reaction conditions.

The form in which the catalyst is used is preferably as anhydrous as possible. Supported palladium catalysts are often commercially available only in hydrous form. The water can be removed from such hydrous catalysts by first washing them with a water-miscible solvent, e.g. a lower alcohol, and then treating them with a product intrinsic to the system, e.g. a succinic acid derivative such as dimethyl succinate. If water is present in the reaction system, this leads to cleavage of the anhydride group in the tetrahydroisobenzofurandione used and/or in the isobenzofurandione formed and hence to the undesirable formation of by-products.

If the process according to the invention is carried out in a liquid-phase procedure, the catalyst can be used for example in amounts of 1 to 10% by weight of palladium and/or platinum, based on the educt. This amount is preferably 2 to 8% by weight. In the case of a trickle-phase procedure, it is possible e.g. to pass 50 to 300 ml/hour of starting mixture over one litre of supported catalyst.

Examples of suitable maleic acid derivatives are maleic anhydride, maleimides, maleamic acid and alkyl maleates. Maleic anhydride and dimethyl and diethyl maleates are preferred, dimethyl maleate being very particularly preferred.

The maleic acid derivative in question can be used for example in an amount of 180 to 220 mol %, based on the educt. This amount is preferably 190 to 210 mol %, especially 195 to 205 mol %.

The process according to the invention is carried out at temperatures of 120° to 300° C., preferably at 130° to 250° C. In the liquid-phase procedure, the rate of temperature increase in the first heating stage from room temperature up to 80° to 110° C. is of no particular significance. Above 80° to 110° C., the temperature is increased at a rate of 0.6° to 3° C. per minute, preferably 0.8° to 2.0° C. per minute. Rates of temperature increase of less than 0.6° C. per minute reduce the yield obtainable (see Comparative Example 1). Rates of temperature increase of more than 3° C. per minute would incur uneconomically high equipment costs on the industrial scale.

The pressure during the reaction is not critical and can be e.g. 1 to 10 bar, preferably normal pressure to 3 bar. It is particularly preferable to carry out the reaction at temperatures of up to 210° C. at normal pressure.

If the process according to the invention is carried out batchwise, the reaction has generally ended after 1 to 4 hours. For the trickle-phase procedure, the catalyst loads indicated above are such that virtually complete conversion is achieved in one pass.

The mixture present after completion of the reaction can be worked up for example in the following manner: Any catalyst present is first separated off and the succinic acid derivative formed from the maleic acid derivative is then removed, e.g. by distillation at reduced pressure. The isobenzofurandione formed, which has for example the formula (II):

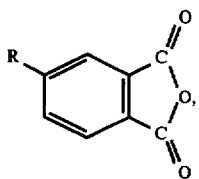

(II)

in which R is as defined for the formula (I), then often remains in sufficiently pure form to be directly re-usable. It can be further purified, e.g. by distillation, if required.

The process according to the invention has a number of surprising advantages. Thus it was to be assumed that maleic acid derivatives would react with the anhydride group of the tetrahydroisobenzofurandione at the high reaction temperatures. The possibility of this reaction is excluded in the process according to C.A. 108:37393e because said process uses only esters and not, as according to the invention, at least one anhydride.

It was further to be expected that the maleic acid derivative, as a dienophile, would react with the intermediate from the dehydrogenation, namely the dihydro derivative of diene structure, in a Deils-Alder reaction.

Surprisingly, both secondary reactions occur only to a negligible extent and the desired dehydrogenation product is obtained in the process according to the invention with yields well above those of 85 to 87% of theory achievable hitherto, being generally in excess of 95% of theory.

No gases have to be handled in the process according to the invention, so no safety technology or disposal costs are incurred.

The succinic acid derivatives formed as coupling products represent valuable chemical intermediates which can be used as readily biodegradable compounds for diverse purposes, e.g. as solvents, as components for the preparation of polyesters and as intermediates for organic pigments.

Finally, it is surprising that not only the desired isobenzofurandiones but also the secondary products of hydrogen uptake, namely the succinic acid derivatives, are formed with a high yield and selectivity. The process according to the invention produces virtually no waste products, which would have to be disposed of, so it is particularly advantageous from the ecological point of view.

EXAMPLES

Example 1

144 g of dimethyl maleate and 83 g of distilled 5-methyltetrahydroisobenzofuran-1,3-dione were placed in a reaction vessel at room temperature.

7.7 g of a commercial catalyst containing 5% by weight of palladium-on-charcoal and having a water content of 52% by weight were suspended in methanol, filtered off with suction, washed with methanol, then treated with dimethyl succinate and washed again with dimethyl succinate. This anhydrous catalyst moistened with dimethyl succinate was added to the above reaction mixture. The resulting mixture was then heated to 110° to 120° C. under a gentle stream of nitrogen, with stirring, and heated further to 205° C. with a temperature increase of 1° C. per minute. The reaction mixture was subsequently stirred at 200° to 205° C. for 1.5 hours. It was then cooled, the catalyst was filtered off with suction and the filtrate was distilled. At 30 mbar, dimethyl succinate was distilled off with a boiling point of 96° to 98° C. (purity above 99.3% by weight). The distillation residue had a 5-methyl-isobenzofuran-1,3-dione content of over 96% by weight. The yield was 97% of theory. The 5-methyl-isobenzofuran-1,3-dione was distilled and obtained in very pure form with a boiling point of 177° C. at 30 mbar.

Example 2

10 ml/hour of a solution of 1 mol of 5-methyl-tetrahydroisobenzofuran-1,3-dione and 2 mol of dimethyl maleate were pumped at 200° C. into the top of a trickle-phase reactor filled with 100 ml of catalyst in tablet form (5% by weight palladium-on-aluminium oxide). The conversion of the dimethyl maleate after passage through the reactor was 100%. No dimethyl fumarate could be detected in the product mixture leaving the reactor. 5-Methylisobenzofuran-1,3-dione and dimethyl succinate had been formed with selectivities of over 95% and over 97% respectively. The conversion of the dehydrogenation was 99.8%. The catalyst showed no signs of deactivation after 500 hours of operation.

Comparative Example 1

The procedure was as in Example 1 except that further heating above 120° C. was carried out at a rate of 0.5° C. per minute. This reduced the yield of 5-methyl-isobenzofuran-1,3-dione to 94% of theory.

Comparative Example 2

The procedure was as in Example 1 except that undistilled 5-methyltetrahydroisobenzofuran-1,3-dione was used. This markedly reduced the reaction rate. After stirring for 4 hours at 205° C., the conversion of 5-methyltetrahydroisbenzofuran-1,3-dione was only 95% and the yield of 5-methyl-isobenzofuran-1,3-dione was only 92% of theory.

What is claimed is:

1. Process for the preparation of an isobenzofurandione by the dehydrogenation of a tetrahydroisobenzofurandione in the presence of a catalyst at elevated temperature, characterized in that a solution of a distilled tetrahydroisobenzofurandione and a maleic acid derivative selected from the group consisting of maleic anhydride, maleimides, maleamic acid and alkyl maleates is contacted with a supported palladium catalyst, a supported platinum catalyst or both in a trickle-phase process at a temperature of 120° to 300° C.

2. Process according to claim 1, wherein tetrahydroisobenzofurandiones of the formula (I):

are used, in which

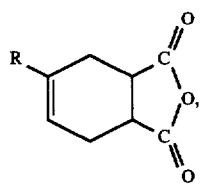

R represents hydrogen or $C_1$–$C_6$-alkyl, and isobenzofurandiones of the formula (II):

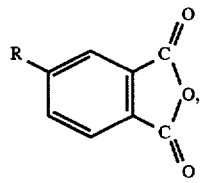

are obtained.

3. Process according to claim 1, characterized in that the catalysts used contain 0.1 to 10% by weight of palladium and/or platinum on aluminium oxide, silicon dioxide, silicic acid, kieselguhr, silicates or charcoal.

4. Process according to claim 1, wherein 50 to 300 ml/hour of starting mixture is passed over 1 of supported catalyst.

5. Process according to claim 1, characterized in that the maleic acid derivative is used in an amount of 180 to 220 mol %, based on the educt.

6. Process according to claim 1, characterized in that it is carried out at pressures in the range 1 to 10 bar.

7. Process according to claim 1, characterized in that the mixture present after the reaction is worked up by a process in which any catalyst present is first separated off and the succinic acid derivative formed from the maleic acid derivative is then distilled off by distillation at reduced pressure.

8. Process for the preparation of an isobenzofurandione by the dehydrogenation of a tetrahydroisobenzofurandione in the presence of a catalyst at elevated temperature, characterized in that a distilled tetrahydroisobenzofurandione is heated to temperatures of between 120° and 300° C. in the presence of a supported palladium catalyst, a supported platinum catalyst or both, and in the presence of a maleic acid derivative selected from the group consisting of maleic anhydride, maleimides, maleamic acid and alkyl maleates in a liquid-phase process, wherein, when the temperature is being increased to reaction temperature, it is increased at a rate of from 1.0° to 3° C. per minute as the temperature passes through the range of from above 80° to 110° C.

* * * * *

UNITED STATES PATENT AND TRADEMARK OFFICE
CERTIFICATE OF CORRECTION

PATENT NO. : 5,672,719
DATED       : September 30, 1997
INVENTOR(S) : Kasbauer, et al.

It is certified that error appears in the above-indentified patent and that said Letters Patent is hereby corrected as shown below:

Col. 5, last line   After " over 1 " insert -- litre --

Signed and Sealed this

Twenty-fourth Day of August, 1999

Attest:

Q. TODD DICKINSON

*Attesting Officer*         *Acting Commissioner of Patents and Trademarks*